United States Patent
Kondo

(12)
(10) Patent No.: US 6,656,464 B2
(45) Date of Patent: *Dec. 2, 2003

(54) GASTRIC EMPTYING-PROMOTING COMPOSITION

(75) Inventor: Takaharu Kondo, Kani (JP)

(73) Assignee: Amano Pharmaceutical Co., Ltd., Aichi (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

This patent is subject to a terminal disclaimer.

(21) Appl. No.: 09/216,857

(22) Filed: Dec. 21, 1998

(65) Prior Publication Data

US 2002/0018773 A1 Feb. 14, 2002

(30) Foreign Application Priority Data

Jul. 2, 1998 (JP) .......................................... 10-204292

(51) Int. Cl.⁷ .............................................. A61K 38/46
(52) U.S. Cl. ........................ 424/94.6; 424/9.1; 435/198
(58) Field of Search .......................... 435/198; 424/9.1, 424/725, 195.15, 94.6, 91

(56) References Cited

U.S. PATENT DOCUMENTS

| | | | | |
|---|---|---|---|---|
| 4,707,364 A | * | 11/1987 | Barach et al. ................. | 426/36 |
| 5,075,231 A | * | 12/1991 | Moreau et al. ............. | 435/198 |
| 5,436,003 A | * | 7/1995 | Rohde et al. .............. | 424/94.2 |
| RE35,218 E | * | 4/1996 | Becker et al. ............... | 514/214 |
| 5,668,117 A | * | 9/1997 | Shapiro ........................ | 514/55 |
| 5,683,697 A | * | 11/1997 | Tani et al. ................ | 424/195.1 |
| 5,691,181 A | | 11/1997 | Lowe | |
| 5,858,755 A | * | 1/1999 | Lowe et al. ................. | 435/198 |
| 6,013,680 A | * | 1/2000 | Ogawa et al. | |

FOREIGN PATENT DOCUMENTS

| | | |
|---|---|---|
| DE | 2 040 425 | 2/1972 |
| DE | 43 32 985 | 3/1995 |
| GB | 1 442 677 | 7/1976 |
| WO | wo 91/18923 | 12/1991 |

OTHER PUBLICATIONS

The Merck Index. An Encyclopedia of Chemicals, Drugs and Biologicals. 12 th Edition. Merck & Co., Inc., 1996, pp. 383, 390, 1174.*
De Boeck et al. J. Pediatr. Gastroenterol. Nutr. 1998, 26(4), pp. 408–411.*
Toida et al. Bioscience, Biotechnology and Biochemistry. Apr. 1998, vol. 62, No. 4, pp. 759–763.*
Chenise Traditional Formulas product "Chzyme". Health Concerns, Oakland CA 94621.*
Hubbard et al. The American Journal of Clinical Nutrition. Nov. 1980. vol. 33, pp. 2281–2286.*
Gow et al. The Lancet. Nov. 14, 1981, pp. 1071–1074.*
Ogawa et al. Shoka to Kyushu (1998), 21 (2), pp. 12–15.*
Gaeddert A. In: "Chinese Herbs in the Western Clinic". Published in 1994. ISBN: 0–9638285–0–9. Reprint from http://www.acupuncturetoday.com/archives2001/oct/10gaedder.html; pp. 1–5.*
Zentler–Munro et al. Pancreas. 1992. vol. 7, No. 3, pp. 311–319.*
Kakiuchi Yuji; Patent Abstracts of Japan, vol. 1997, No. 6, Feb. 25, 1997, JP 09 052845 A, Amano Pharmaceutical Co.
Plucinski et al; "Fat Digestion in Rat: Role of Lingual Lipase", 1979 The American Physiological Society, pp E541–E547.

* cited by examiner

Primary Examiner—Sandra E. Saucier
Assistant Examiner—Vera Afremova
(74) Attorney, Agent, or Firm—Sughrue Mion, PLLC

(57) ABSTRACT

Compositions having an effect of promoting gastric emptying. These compositions comprise a lipase which was found to have an effect of promoting gastric emptying together with lipase activity-free ingredient(s) acting on the digestive tracts such as a prokinetic, a histamine $H_2$ receptor antagonist, a proton pump inhibitor and/or a stomachic ingredient. They are efficaciously employed as medicaments for ameliorating or treating chronic gastrointestinal symptoms such as sinking feelings, heartburn and heaviness in the stomach, i.e., complaints about the digestive tracts.

13 Claims, 3 Drawing Sheets

GASTRIC EMPTYING-PROMOTING COMPOSITION

FIELD OF THE INVENTION

This invention relates to compositions having an effect of promoting the gastric emptying. More particularly, it relates to medicaments containing a lipase preparation which is a digestive enzyme. The medicaments of the present invention are efficaciously used in ameliorating or treating chronic gastrointestinal symptoms such as sinking feelings, heartburn and heaviness in the stomach, i.e., complaints about the digestive tracts.

BACKGROUND OF THE INVENTION

Even healthy people often notice subjective gastric symptoms (sinking feelings, heartburn, anorexia, etc.) in the everyday life. These symptoms are caused by stress, overeating, excessive intake of alcoholic drinks and intake of drugs. Moreover, it is frequently observed that the stress of the complicated current social structure or side effects of medicaments result in chronic gastrointestinal symptoms such as sinking feelings and heaviness in the stomach, i.e., complaints about the digestive tracts, which is now a serious social problem.

In the present aging society, furthermore, the aged are largely affected by the above-mentioned problem.

Additional major causes of the complaints about the digestive tracts include maldigestion, chronic gastritis, delayed gastric emptying after meals, gastric hyperacidity and peptic ulcers which bring about subjective symptoms such as abdominal swelling feelings, unpleasantness in the upper abdomen, anorexia, heartburn and belching (eructation). To ameliorate these symptoms, there have been employed various agents adequate for the respective symptoms. To treat delayed gastric emptying, there have been developed and employed acetylcholine agonists (aclatonium napadisilate preparations), antidopamine agents (domperidone preparations), serotonin antagonists (cisapride preparations), opiate agonists (trimebutine maleate preparations) and ursodeoxycholic acid preparations.

To treat gastric hyperacidity, use has been made of antacid agents, pepsin inhibitors, gastric mucosa protective agents, anticholine agents for suppressing the secretion of gastric hydrochloric acid, parasympathetic blocking agents, histamine $H_2$ receptor antagonists (hereinafter referred to as "$H_2$ blockers"), proton pump inhibitors, etc. Examples of the $H_2$ blockers include cimetidine, ranitidine and famotidine, while examples of the proton pump inhibitors include omeprazole, lansoprazole and raveprazole.

However, acetylcholine agonists, etc. have only less selective pharmacological actions. Moreover, there is a large problem regarding the side effects of these agents, i.e., acting on the central nervous system. Other agents might also cause diarrhea, loose stool, abdominal pain, retching, vomiting, etc. as side effects thereof. In these cases, it is needed to stop the administration of the agents or reduce the dose thereof. These agents are administered so frequently in many cases that they should have high safety.

In general, aged persons are liable to have abdominal swelling feelings after taking fat-rich meals. Also, the food intake of aged persons goes down day by day. These phenomena are seemingly caused by the delayed gastric emptying. In the case of these aged, in particular, it is feared that the above-mentioned side effects of agents might result in serious problems. Therefore, these agents should be administered to them very cautiously.

SUMMARY OF THE INVENTION

Based on the above consideration, the present inventor has conducted extensive studies. As a result, it has been found that lipase (i.e., a kind of digestive enzyme) exhibits not only a direct effect on foods to accelerate the digestion but also an unexpected effect of promoting the gastric emptying, thus completing the present invention.

It is said that the gastric emptying action is fed back by fatty acids, which are formed by the hydrolysis of lipids, and thus the discharge of the gastric contents is delayed. However, it has been found out that a lipase preparation unexpectedly promotes the gastric emptying action when taken together with foods containing lipids.

Accordingly, the present invention relates to gastric emptying-promoting agents comprising lipase as the active ingredient; a method for promoting gastric emptying by administering lipase; and use of lipase for the manufacture of a medicament for promoting gastric emptying. It is expected that the compositions containing a lipase preparation according to the present invention not only accelerate the digestion of foods but also promote the gastric emptying to thereby ameliorate various subjective symptoms. Thus, these compositions are useful in treating the pathological conditions as cited above.

DETAILED DESCRIPTION OF THE INVENTION

Figure 1:
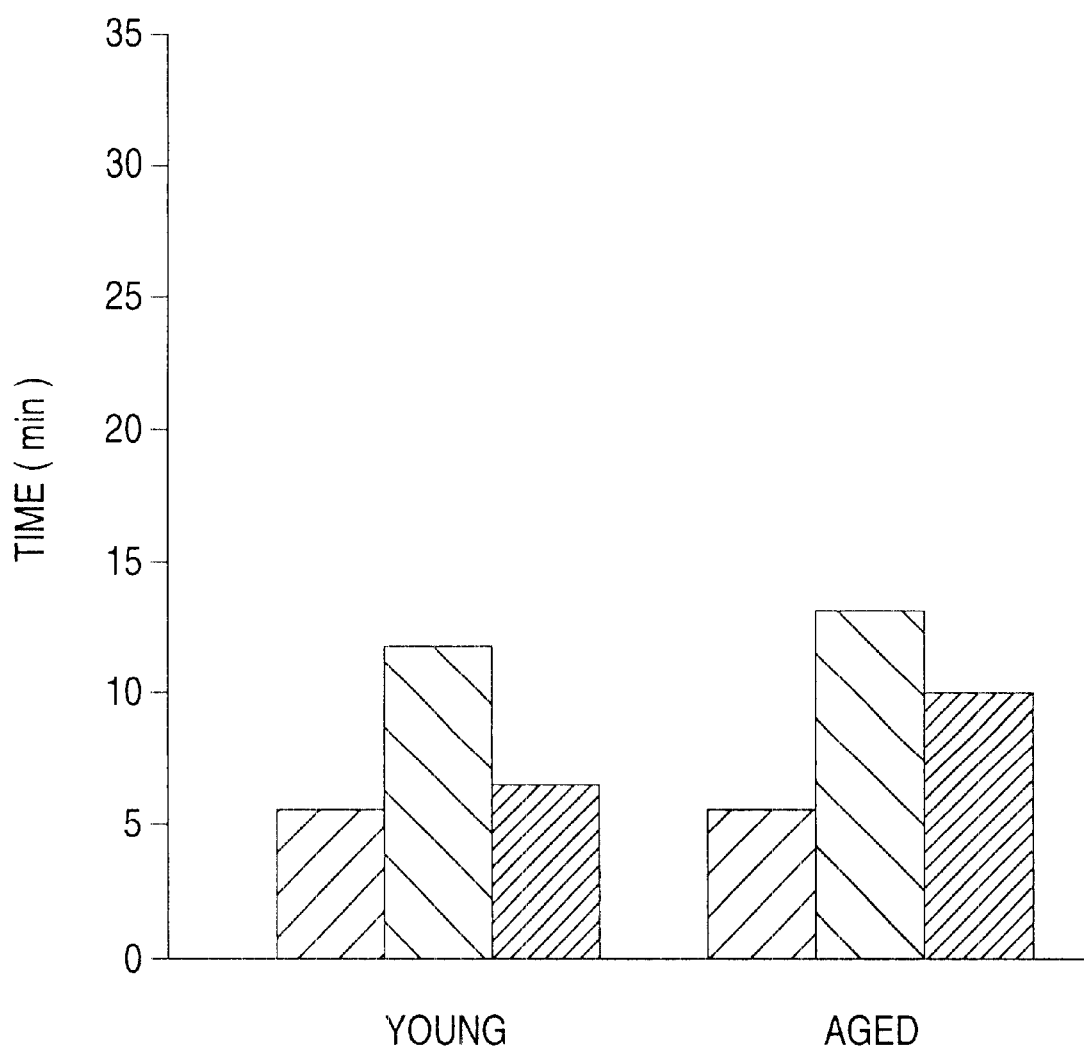
FIG. 1 is a graph showing the results of the determination of 25% emptying time in Example 1, wherein the bars indicate the data of the control meal, the fat-enriched meal and the fat-enriched meal+lipase preparation (from left to right), respectively.

The lipase to be used in the present invention may be an arbitrary enzyme or enzyme preparation, so long as it can act at the gastric pH value so as to digest lipids. It is preferable to use an enzyme preparation showing a digestive effect on lipids as its major action.

When foods are put into the stomach, the gastric pH value is elevated usually to 3 to 5. Although the lipase preparation usable herein varies depending on the gastric pH conditions in the case where the preparation is to be used, use can be made therefor of commonly marketed lipase preparations for medicinal purposes.

Marketed lipase preparations for medicinal use include various ones originating in animals and microorganisms. In the present invention, it is preferable to use lipases originating in microorganisms. More particularly, preferable examples thereof include Lipase AP4, Lipase AP6, Lipase AP12, Lipase M-AP5, Lipase M-AP10 and Lipase M-AP20 (manufactured by Amano Pharmaceutical Co., Ltd.), Lipase Saiken (manufactured by Osaka Saikin Kenkyusho), Lipase MY (manufactured by Meito Sangyo). It is also possible to use enzyme preparations having the lipase activity. For example, use can be made of mixed digestive enzyme preparations such as Biodiastase, Biodiastase 500, Biodiastase 700, Biodiastase 1000, Biodiastase 2000, Pancreatin, Pancreatic Digestive Enzyme TA and Pancreatic Digestive Enzyme 8AP (manufactured by Amano Pharmaceutical Co., Ltd.), Biotamylase, Biotamyolase S, Biotalase A-1000, Biotalase P-1000 and Denapsin 10 (manufactured by Nagase Seikagaku Kogyo), Cellulosin AP and Prolicin (manufactured by Ueda Kagaku), Takadiastase (manufactured by Sankyo), Sumizyme (manufactured by Shin Nippon Kagaku Kogyo) and Biotamylase (manufactured by Nagase Sangyo). It is still preferable to use Lipase AP4, Lipase AP6, Lipase AP12, etc. therefor.

In the present invention, it is also possible to use a lipase activity-free ingredient acting on the digestive tracts. More particularly speaking, the present invention provides compositions containing stomachic crude drugs, prokinetics, $H_2$ blockers, proton pump inhibitors, etc. together with a lipase preparation.

The above-mentioned lipase may be appropriately combined with stomachic crude drugs; cisapride preparations, etc. which have been employed as prokinetics; cimetidine, etc. which have been employed as $H_2$ blockers; or omeprazole preparations, etc. which have been employed as proton pump inhibitors. Moreover, these ingredients may be appropriately combined with each other. In the present invention, the combined use of these ingredients can exert elevated effects and decrease the dose of medicaments having side effects, thus largely relieving the side effects. Consequently, it is possible to obtain highly safe medicinal compositions which can be administered over a prolonged period of time.

Examples of the stomachic crude drugs usable in the present invention include aniseed, aloe, fennel, turmeric, linderae radix, amethystanthi herba, scutellaria root, phellodendron bark, coptis rhisome, processed garlic, agastachis herba, calamus root, dry ginger, citri immatuarus fructus, immature orange, cinnamon bark, gentian, red ginseng, magnolia bark, evodiae fructus, pepper, columbo, condurango, zanthoxylum fruit, kaempferiae rhizoma, perilla seed, amomum seed, ginger, cardamon, green tangerine peel, Japanese sweetflag, centaurium, swertia herb, atractylodes lancea, perilla herb, star anise fruit, rhubarb, panax rhizome, clove, citrus unshiu peel, capsicum, bitter orange peel, animal liver, picrasma wood, nutmeg, ginseng, mentha herb, long pepper, atractylodes rhizome, hop, nux vomica extract, bucbean leaf menyanthes, saussurea root, bitter cardamon, Japanese entian, alpiniae offcinarum rhizoma, lemon oil, 1-menthol and dl-menthol.

Examples of the prokinetics include acetylcholine agonists, antidopamine agents, serotonin antagonists, opiate agonists and ursodeoxycholic acid preparations.

Examples of the $H_2$ blockers include cimetidine, ranitidine and famotidine, while examples of the proton pump inhibitors include omeprazole, lansoprazole and raveprazole.

The amount of the lipase preparation is not particularly restricted, so long as the lipase thus employed can exert an effect of promoting the gastric emptying. Although lipase is employed usually in the standard amount as specified below, the effects of the present invention can be achieved even though the lipase content is lower than the standard level.

In accordance with the General Test Methods defined in The Pharmacopocia of Japan (13th revised), a single dose of a lipase expressed in the activity is 300 U or more in terms of fat-digestibility. When determined by the United States Pharmacopeia (USP) method or the Federation International Phamaceutique (FIP) method, this activity corresponds respectively to fat-digestibility of about 1,600 U or more (USP) and about 2,100 U or more (FIP).

In the present invention as described above, the conventional stomachic crude drugs may be used within a pharmaceutically acceptable range. Alternatively, the compositions of the present invention may be in the form of Chinese herbal and crude drug preparations which are exemplified by anchusan, heiisan, koshaheiisan, shinbuto, shikunshito, shokyoshashinto, ninjinto, hangebyakujutsutenmato, hangeshashinto, bukuryoin, rikkunshito and taikininshi.

In addition, the conventional agents for improving the digestive motion can be used in a reduced amount. For example, the daily dose of a cisapride preparation (product name: Acenalin tablets), which is generally administered in a dose of 7.5 to 20 mg/day, can be lowered to about 0 to 10 mg/day when used together with a lipase preparation. Similarly, the dose of $H_2$ blockers or proton pump inhibitors can be reduced in the combined use with a lipase preparation.

With respect to the general dose of the $H_2$ blocker, cimetidine may be used from about 400 mg/day to about 800 mg/day, ranitidine may be used from about 150 mg/day to about 300 mg/day, and famotidine may be used from about 20 mg/day to about 40 mg/day. With respect to the general dose of the proton pump inhibitor, omeprazole, lansoprazole, raveprazole, etc. may be used from about 20 mg/day to about 60 mg/day. These doses can also be reduced to the half or less when used together with a lipase preparation.

These ingredients may be administered together to a living body. Alternatively, they may be processed into separate preparations and then combined at using. Also, a conventional stomachic crude drug, prokinetic, etc. may be processed into a single preparation together with a lipase preparation. In producing these preparations, other active ingredients may be employed, if necessary, while taking the incompatibility of the ingredients into consideration. Needless to say, various auxiliaries may be employed for producing these preparations.

These compositions may be provided in various forms. As described above, stomachic crude drugs, prokinetics, $H_2$ blockers, etc. and lipase preparations may be processed into separate preparations and then combined before administration. Alternatively, these active ingredients may be used together to give a single medicament preparation.

These agents may be in arbitrary dosage forms (liquids, capsules, granules, pills, suspensions, emulsions, powders, tablets, syrups, limonades, chewables, etc.), so long as the active ingredients contained therein can exert their effects. It is considered that powders, granules, chewables, etc. are preferable in, for example, the refreshing feel at or after using.

To further illustrate the present invention in greater detail, the following Test Examples and Examples will be given. However, the present invention is not restricted thereto but to be understood in a broad sense wherein one skilled in the art can easily accomplished the same.

EXAMPLE 1

A fat-enriched meal was given to groups of young and aged subjects. Then these groups were compared with each other in subjective symptoms, gastric emptying time and lunch intake.

The subjects involved 5 normal young peoples (average age: 23±1.4) and 6 normal aged peoples (average age: 73±4.0) each having no past history of digestive diseases. The gastric emptying time was measured by the electrical impedance tomography (EIT) with the use of an APT system DAS-01P developed in Sheffield University.

The test meals were each a liquid food (400 ml). A control meal was a consomme (salt content: 0.65%, containing no fat) while the fat-enriched meal was a consomme soup containing margarine (fat-enriched soup containing 24.6 g of fat). To examine the effect of the digestion of fat by lipase, 240 mg of Lipase AP12 (manufactured by Amano Pharmaceutical Co., Ltd.) was administered together with the fat-enriched soup. Table 1 summarizes the results wherein each value is expressed in "mean±standard error (SE)".

TABLE 1

| Test meal | 25% Emptying time (min) | | 50% Emptying time (min) | |
| --- | --- | --- | --- | --- |
| | Young | Aged | Young | Aged |
| control | 5.3 ± 0.9 | 5.8 ± 1.1 | 15.2 ± 3.0 | 15.8 ± 6.3 |
| fat-enriched | 12.0 ± 3.4 | 13.2 ± 3.5 | 19.1 ± 3.3 | 28.0 ± 6.1 |
| fat-enriched + lipase | 6.5 ± 1.2 | 9.8 ± 2.3 | 13.8 ± 1.9 | 18.4 ± 3.5 |

Figure 2:
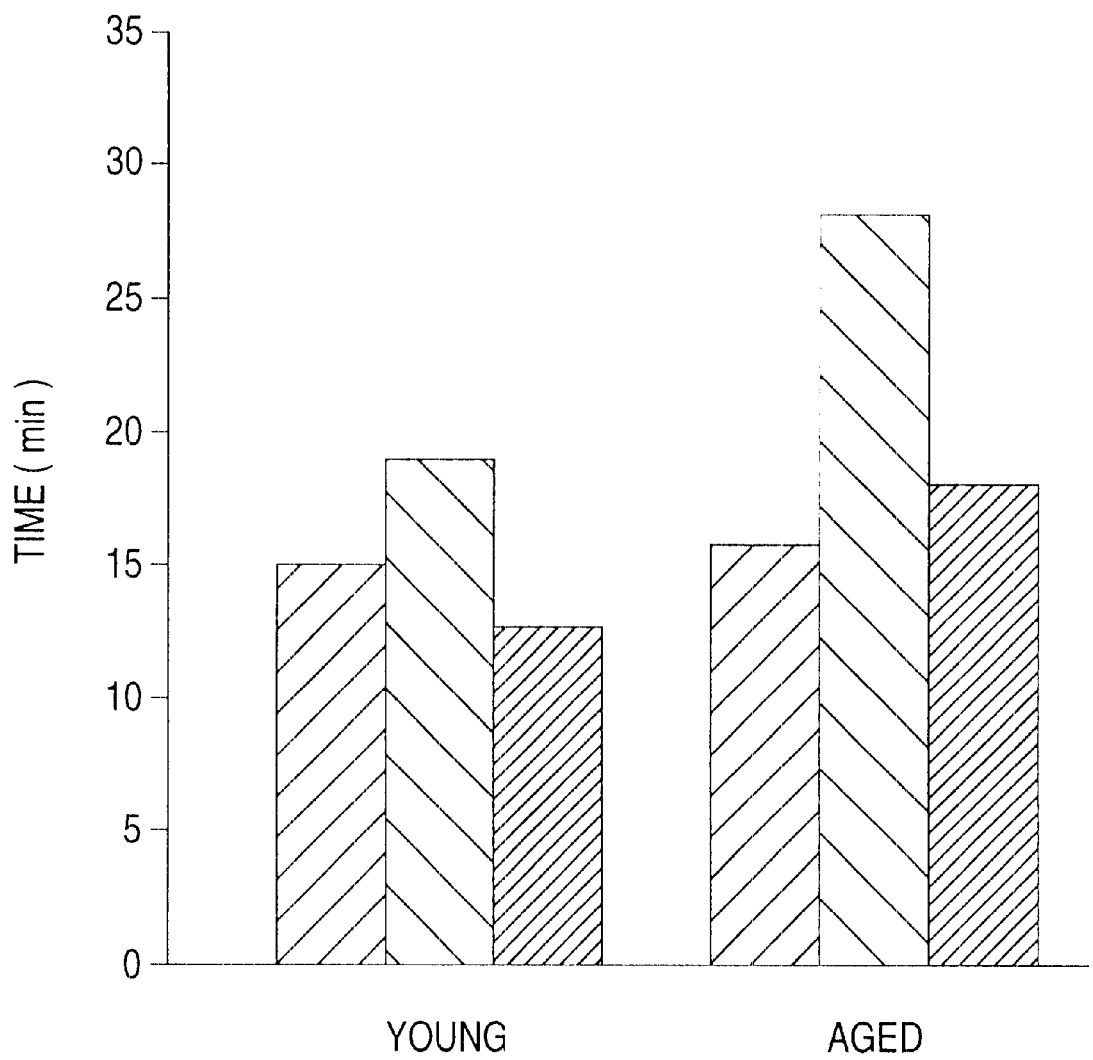
FIG. 2 is a graph showing the results of the determination of 50% emptying time in Example 1, wherein the bars indicate the data of the control meal, the fat-enriched meal and the fat-enriched meal+lipase preparation (from left to right), respectively.

FIGS. 1 and 2 illustrate the data given in Table 1.

Thus, there is observed a tendency that gastric emptying time was significantly prolonged by enriching the meal with fat but this prolonged period was shortened by lipase administration. The 50% gastric emptying times of the consomme showed no difference between the young group and the aged group. In both groups, the 50% gastric emptying times of the fat-enriched soup were longer than those of the consomme. In the aged group, the 50% gastric emptying time was significantly prolonged. It is clarified that by taking the lipase, the 50% gastric emptying times were considerably improved in both of the young and aged groups. Namely, it is considered that the gastric emptying time is prolonged by enriching the meal with fat and this effect is accelerated by aging. It seems that the administration of a lipase preparation is efficacious in ameliorating the delayed gastric emptying following fat intake.

EXAMPLE 2

Figure 3:
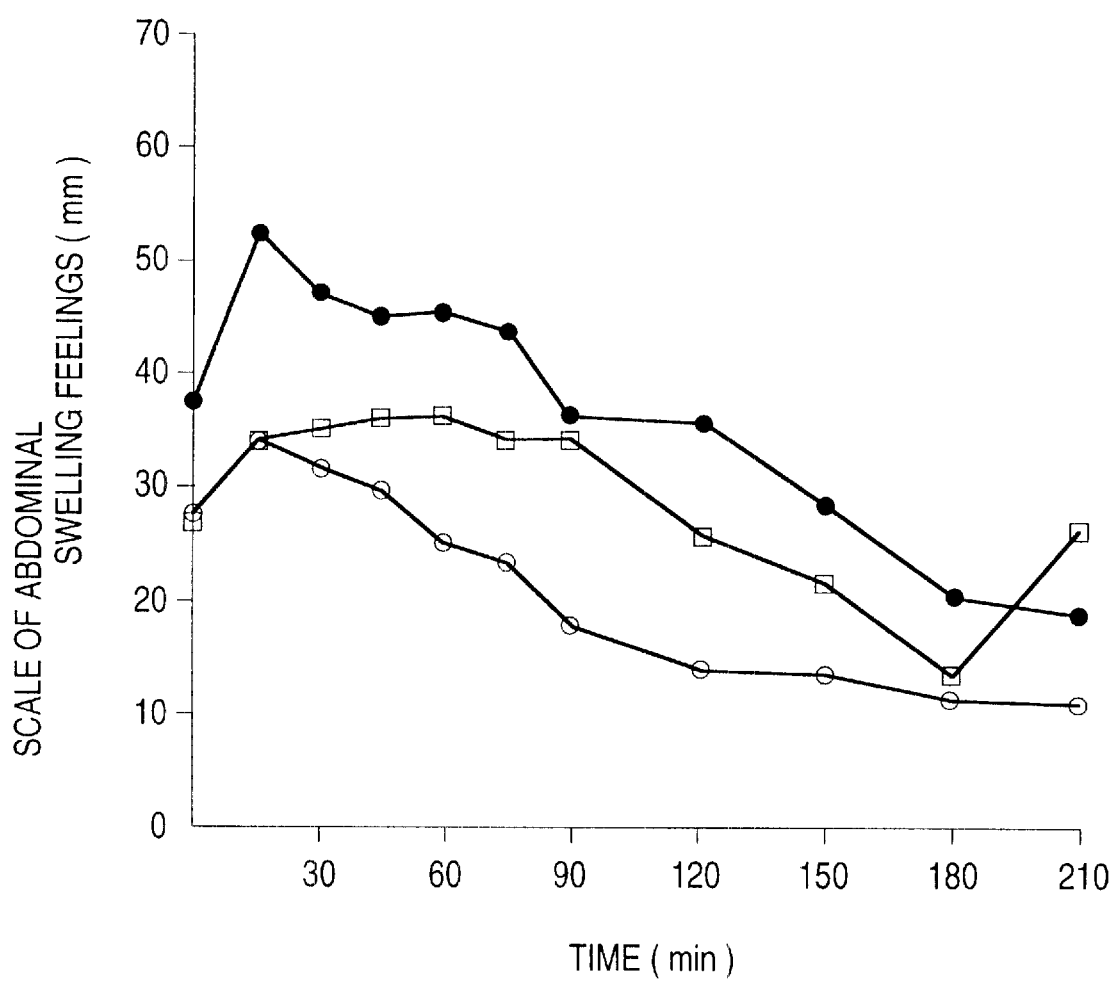
FIG. 3 is a graph showing the results of Example 2, wherein -●-, -□- and -○- show the data of the fat-enriched meal, the fat-enriched meal+lipase preparation and the control meal, respectively.

Similar to Example 1, 3 young subjects and 3 aged subjects took each test meal. Then the abdominal swelling feelings were measured as a subjective symptom by using a visual analogue scale. In this method, 10 cm scales were given to the subjects. Then the subjects themselves noted the level of the abdominal swelling feelings in the scales at intervals of 15 or 30 minutes. FIG. 3 shows the results.

FIG. 3 indicates that the fat-enriched meal gave long-lasting abdominal swelling feelings, compared with the control meal, and the administration of the lipase preparation relieved the abdominal swelling feelings. Namely, the gastric emptying was accelerated by the lipase preparation.

EXAMPLE 3

Combined Use of Prokinetics with Lipase Preparation

Six panelists (A to F) suffering from chronic gastrointestinal symptoms such as abdominal (stomach) pain, sinking feelings, heartburn, vomiturition or abdominal swelling feelings were divided into the following 3 groups and the ameliorating effects were judged.

Group 1 (A and B):
 2 tablets of Acenalin (2.5 mg) after every meal.
Group 2 (C and D):
 1 tablet of Acenalin (2.5 mg)+Lipase AP12 (60 mg) after every meal.
Group 3 (E and F):
 Lipase AP12 (60 mg) after every meal.

Each subjects had usual meals for 1 week under the conditions as specified above and the amelioration in the chronic gastrointestinal symptoms was monitored. Table 2 shows the results.

TABLE 2

| | Group 1 | | Group 2 | | Group 3 | |
| --- | --- | --- | --- | --- | --- | --- |
| | before | after | before | after | before | after |
| Symptom | A  B | A  B | C  D | C  D | E  F | E  F |
| abdominal (stomach) pain | —  3 | —  6 | 0  3 | 3  13 | 3  — | 13  — |
| sinking feeldings | 3  3 | 6  13 | 3  0 | 6  10 | 3  0 | 3  3 |
| heartburn | 0  0 | 3  10 | 3  0 | 13  10 | 0  0 | 10  3 |
| eructation | 0  0 | 3  3 | 3  — | 6  — | 3  3 | 6  3 |
| vomiturition | —  3 | —  6 | 3  3 | 6  6 | —  3 | —  6 |
| abdominal swelling feelings | 3  0 | 3  3 | 0  3 | 3  6 | 3  0 | 6  3 |

In the above Table 2, the severity of each symptom is expressed according to the following criteria.

Before administration:
 –: No symptom is observed.
 3 : The symptom is sometimes observed.
 0 : The symptom is observed.
After administration:
 10: The symptom is completely ameliorated.
 3: The symptom is ameliorated.
 0: No change is observed.
 –3: The symptom is worsened.

As Table 2 clearly shows, the above symptoms were ameliorated in all of the groups 1 to 3. In the group 2, remarkable ameliorating effects were observed though the dose of Acenalin was halved. No side effect was observed.

EXAMPLE 4

$H_2$ Blocker or Proton Pump Inhibitor with Lipase Preparation

Eight panelists (G to N) suffering from chronic gastrointestinal symptoms similar to those described in Example 3 were divided into the following 5 groups and the ameliorating effects were judged.

Group 1 (G):
 cimetidine 200 mg after every meal.
Group 2 (H and I):
 cimetidine 100 mg+Lipase AP12 60 mg after every meal.
Group 3 (J):
 1 tablet of omepral (20 mg) per day.
Group 4 (K and L):
 1 tablet of omepral (20 mg) per day+Lipase AP12 60 mg after every meal.

Group 5 (M and N):

Lipase AP12 60 mg after every meal.

Each subjects had usual meals for 1 week under the conditions as specified above and the amelioration in the chronic gastrointestinal symptoms was monitored. As a result, the above symptoms were considerably ameliorated in all of the groups. In the group 4, in particular, quick ameliorating effects were observed. In the group 2, the ameliorating effects were quickened compared with the group 1, though the dose of the $H_2$ blocker was halved. No side effect was observed.

Because of being efficacious in ameliorating delayed gastric emptying, lipase preparations are expected as useful as gastric emptying-ameliorating agents by which complaints about the digestive tracts can be relieved and the deterioration in the digestive functions can be normalized.

While the invention has been described in detail and with reference to specific embodiments thereof, it will be apparent to one skilled in the art that various changes and modifications can be made therein without departing from the spirit and scope thereof.

This application is based on Japanese patent application No. Hei-10-204292, filed on Jul. 2, 1998, and incorporated therein by reference.

What is claimed is:

1. A gastric emptying-promoting composition consisting essentially of, as an active ingredient, lipase active at gastric pH values so as to digest lipids, wherein said lipase is derived from a microorganism, and is selected from the group consisting of Lipase AP4, Lipase AP6, and Lipase AP12 and at least one substance selected from the group consisting of prokinetics, histamine H2 receptor antagonists, proton pump inhibitors and stomachic crude drugs.

2. A method for promoting gastric emptying in a subject who needs gastric emptying promotion on the basis of gastric emptying time measured by the electrical impedance tomography (EIT) with the use of an APT system DAS-01P developed in Sheffield University, which comprises orally administering together with or after taking a lipid containing food, to said subject:

a lipase active in the stomach to digest lipids, wherein said lipase is derived from a microorganism, and is selected from the group consisting of Lipase AP4, Lipase AP6, and Lipase AP12, said lipase being administered in an amount effective for promoting gastric emptying; and a lipid containing food.

3. The method as claimed in claim 2, which further comprises administering at least one substance selected from the gorup consisiting of prokinetics, histamine, $H_2$ receptor antagonists, proton pump inhibitors and stomachic crude drugs.

4. The method according to claim 2, wherein the subject is a human.

5. A gastric emptying-promoting composition according to claim 1, which consists essentially of, as an active ingredient, lipase active at gastric pH values so as to digest lipids and at least one substance selected from the group consisting of prokinetics, proton pump inhibitors and stomachic crude drugs.

6. A gastric emptying-promoting composition according to claim 1, which comprises a single dose of lipase having an activity of 300 U or more in terms of fat-digestibility of fat containing food.

7. A gastric emptying-promoting method according to claim 2, wherein the lipase is provided in a dose having an activity of 300 U or more in terms of fat-digestibility.

8. A gastric emptying-promoting composition according to claim 1, which comprises a single dose of lipase having an activity of 300 U or more and 240 mg or less.

9. A method according to claim 2, wherein the lipase is provided in a dose having an activity of 300 U or more and 240 mg or less.

10. A method for promoting gastric emptying in a subject who needs gastric emptying promotion on the basis of gastric emptying time measured by the electrical impedance tomography (EIT) with the use of an APT system DAS-01P developed in Sheffield University, which comprises orally administering together with or after taking a lipid containing food, to said subject:

a lipase active in the stomach to digest lipids, wherein said lipase is derived from a microorganism, and is selected from the group consisting of Lipase AP4, Lipase AP6, and Lipase AP12, said lipase being administered in an amount effective for promoting gastric emptying; and the lipid containing food, and which further comprises administering at least one substance selected from the group consisting of prokinetics, histamine H2 receptor antagonists, proton pump inhibitors and stomachic crude drugs.

11. A gastric emptying-promoting composition, which comprises a single dose of lipase having an activity of 300U or more in terms of fat-digestibility of fat containing food, and which consists essentially of, as an active ingredient, lipase active at gastric pH values so as to digest lipids, wherein said lipase is derived from a microorganism, and is selected from the group consisting of Lipase AP4, Lipase AP6, and Lipase AP12, and at least one substance selected from the group consisting of prokinetics, histamine H2 receptor antagonists, proton pump inhibitors and stomachic crude drugs.

12. A gastric emptying-promoting composition, which comprises a single dose of lipase having an activity of 300U or more and 240 mg or less, and which consists essentially of, as an active ingredient, lipase active at gastric pH values so as to digest lipids, wherein said lipase is derived from a microorganism, and is selected from the group consisting of Lipase AP4, Lipase AP6, and Lipase AP12, and at least one substance selected from the group consisting of prokinetics, histamine H2 receptor antagonists proton pump inhibitors and stomachic crude drugs.

13. A method for promoting gastric emptying in a subject who needs gastric emptying promotion on the basis of gastric emptying time measured by the electrical impedance tomography (EIT) with the use of an APT system DAS-01P developed in Sheffield University, which comprises orally administering together with or after taking a lipid containing food, to said subject:

a lipase active in the stomach to digest lipids, wherein said lipase is derived from a microorganism, and is selected from the group consisting of Lipase AP4, Lipase AP6, and Lipase AP12, said lipase being administered in a dose having an activity of 300U or more and 240 mg or less; and the lipid containing food.

* * * * *